United States Patent [19]

Shibata et al.

[11] Patent Number: 5,264,264
[45] Date of Patent: Nov. 23, 1993

[54] PRESSURE-SENSITIVE TAPE, PRESSURE-SENSITIVE TAPE-FIXING STRUCTURE, AND ROLL OF PRESSURE-SENSITIVE TAPE

[75] Inventors: Kazumasa Shibata; Teiji Sakashita; Masaaki Arakawa, all of Osaka, Japan

[73] Assignee: Nitto Denko Corporation, Osaka, Japan

[21] Appl. No.: 801,374

[22] Filed: Dec. 2, 1991

[30] Foreign Application Priority Data

Jun. 28, 1991 [JP] Japan .................. 3-158009

[51] Int. Cl.[5] .................. A61F 13/15; A61F 13/58
[52] U.S. Cl. .................. 428/40; 428/120; 428/124; 428/194; 428/195; 428/212; 428/343; 428/355; 604/389; 604/390
[58] Field of Search .......... 428/40, 194, 195, 212, 428/214, 120, 124, 343, 355; 604/389, 390; 206/411

[56] References Cited

U.S. PATENT DOCUMENTS

| | | | |
|---|---|---|---|
| 3,107,195 | 10/1963 | Stegler | 428/57 |
| 3,257,678 | 6/1966 | Batchelder | 206/411 |
| 3,770,556 | 11/1973 | Evans et al. | 161/39 |
| 4,168,196 | 9/1979 | Nemeth | 428/40 |
| 4,447,485 | 5/1984 | Aritake | 428/144 |
| 4,770,913 | 9/1988 | Yamamoto | 604/390 |

FOREIGN PATENT DOCUMENTS

| | | | |
|---|---|---|---|
| 2647838 | 4/1977 | Fed. Rep. of Germany . | |
| 112007 | 6/1984 | Japan | 604/389 |
| 228004 | 12/1984 | Japan | 604/389 |
| 228005 | 12/1984 | Japan | 604/389 |
| 94536 | 6/1986 | Japan . | |

*Primary Examiner*—Ellis P. Robinson
*Assistant Examiner*—Nasser Ahmad
*Attorney, Agent, or Firm*—Sughrue, Mion, Zinn, Macpeak & Seas

[57] ABSTRACT

A pressure-sensitive tape, a pressure-sensitive tape-fixing structure comprising a member made of a material having a rough surface, having fixed thereto the pressure-sensitive tape, and a roll of the pressure-sensitive tape are disclosed, the pressure-sensitive tape comprising a pressure-sensitive tape comprising a tape substrate, a first pressure-sensitive adhesive area provided on one side of the tape substrate in a tape substrate part which is close to one end of the tape substrate, and a second pressure-sensitive adhesive area provided on one side of the tape substrate in a tape substrate part which is close to the other end of the tape substrate, wherein either or both of said first pressure-sensitive adhesive area and said second pressure-sensitive adhesive area have a strongly adhesive area at an end part thereof to which an external peeling force is to be applied first, and said strongly adhesive area has a peel strength higher than that of the other part of the pressure-sensitive adhesive area.

20 Claims, 4 Drawing Sheets

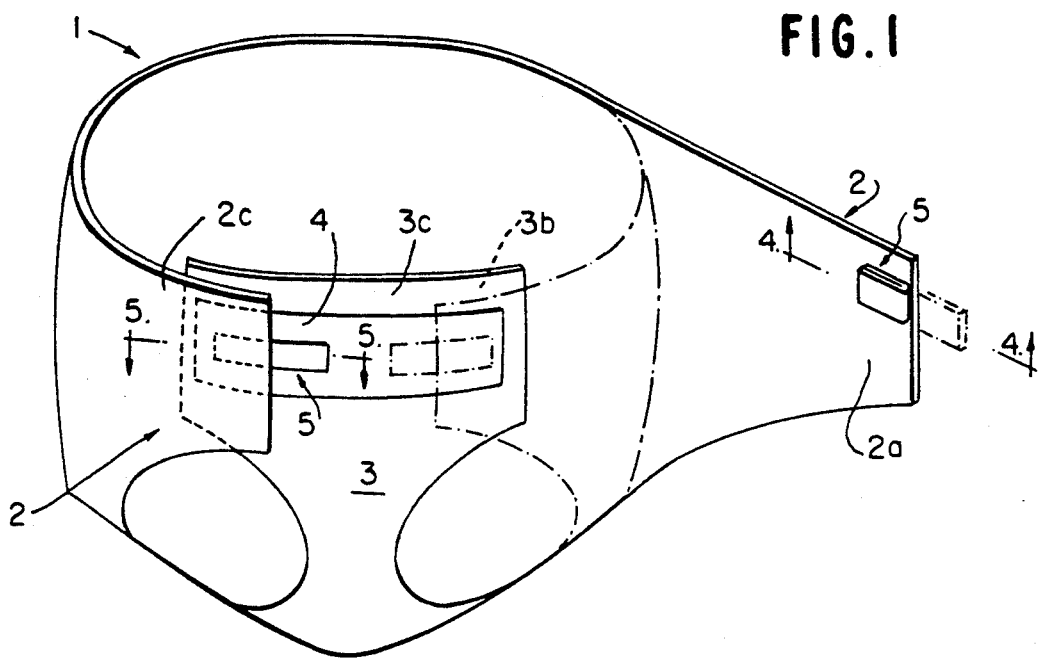
FIG.1
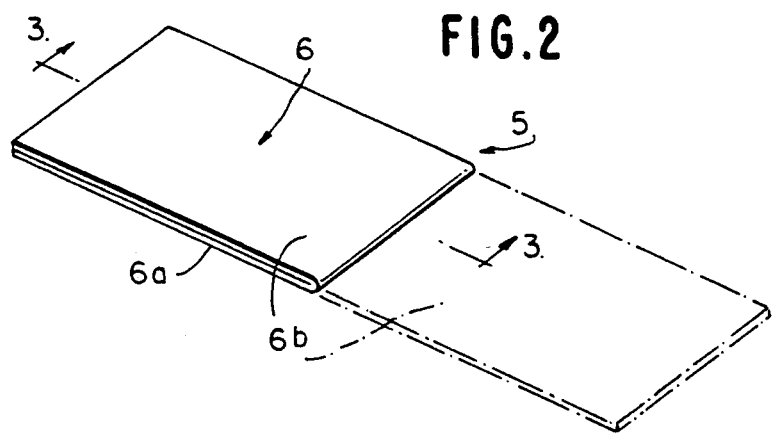
FIG.2
FIG.3
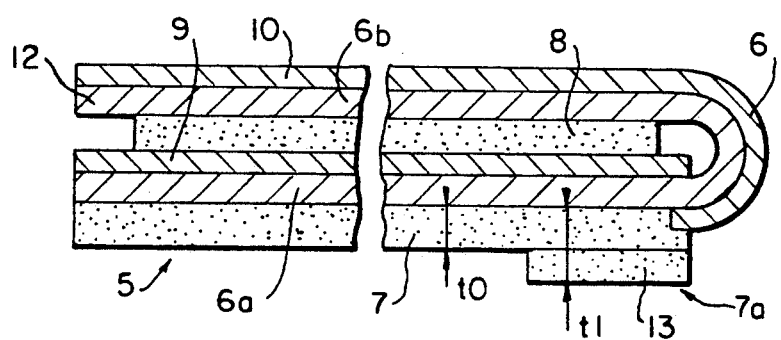

PRESSURE-SENSITIVE TAPE, PRESSURE-SENSITIVE TAPE-FIXING STRUCTURE, AND ROLL OF PRESSURE-SENSITIVE TAPE

FIELD OF THE INVENTION

The present invention relates to a pressure-sensitive tape for use in fixing one member to another member or holding two members together as in, for example, fastener tapes in a diaper which serve to fix a front part of the diaper to the back part thereof. The present invention further relates to a pressure-sensitive tape-fixing structure in which the above pressure-sensitive tape is fixed to a support, and also relates to a roll of pressure-sensitive tape.

BACKGROUND OF THE INVENTION

As described in JP-A-U-61-94536 (the term "JP-A-U" as used herein means an "unexamined published Japanese utility model application") and as shown in FIG. 10, the fastener tape 20 in a conventional diaper 1 comprises a tape substrate 21, a first pressure-sensitive adhesive area 22 provided on one side of the substrate 21 in a substrate part 21a which is close to one end of the substrate 21, and a second pressure-sensitive adhesive area 24 provided on the other side of the substrate 21 in a substrate part 21b which is close to the other end of the substrate 21. The first pressure-sensitive adhesive area 22 is formed by coating the part 21a with a pressure-sensitive adhesive at a uniform thickness over the whole surface and serves to fix the tape substrate 21 to a top sheet 2a in a back part 2 of the diaper 1, while the second pressure-sensitive adhesive area 24 is formed by coating the part 21b with a pressure-sensitive adhesive at a uniform thickness over the whole surface and serves to bond the tape substrate 21 to a center tape 23 provided in a front part 3 of the diaper 1.

The fastener tape 20 receives external peeling forces when an infant or person who is wearing the diaper 1 walks or fingers the back part 2. There are cases where due to such external forces, the fastener tape 20 peels off the back part 2 or other part during use of the diaper 1. Further, there is another problem that when the tape substrate part 21a close to one end of the tape substrate 21 is pulled away from the front part 3 in order to refasten the diaper, the first pressure-sensitive adhesive area 22 peels off the back part 2 by the pulling force.

The above-described undesirable peeling has occurred frequently particularly in diapers in which the fastener tape 20 is bonded to a top sheet 2a in the back part 2, because the top sheet 2a is generally formed by a nonwoven fabric and, hence, the fastener tape 20 shows poor adhesion to this top sheet 2a.

Although the poor adhesion may be improved by increasing the thickness of the pressure-sensitive adhesive layer in the first pressure-sensitive adhesive area 22 or second pressure-sensitive adhesive area 24 in the fastener tape 20 to thereby increase the peel strength from the diaper 1, this expedient is disadvantageous in that the pressure-sensitive adhesive should be used in an increased amount and this raises the cost of diaper production.

SUMMARY OF THE INVENTION

The present invention has been accomplished to overcome the above problems.

Accordingly, one object of the present invention is to provide a pressure-sensitive tape having an increased peel strength without increasing the production cost thereof.

Another object of the present invention is to provide a pressure-sensitive tape-fixing structure in which the pressure-sensitive tape is strongly fixed to even a member made of a material having a rough surface, such as a nonwoven fabric, without increasing the production cost thereof.

Still another object of the present invention is to provide a roll of pressure-sensitive tape having an increased peel strength without increasing the production cost thereof.

BRIEF DESCRIPTION OF THE DRAWINGS

FIG. 1 is a perspective view of a diaper using the pressure-sensitive tape according to the present invention;

FIG. 2 is a perspective view of a fastener tape for use in diapers which is one embodiment of the pressure-sensitive tape according to the present invention;

FIG. 3 is an enlarged sectional view taken on line III—III of FIG. 2;

DETAILED DESCRIPTION OF THE INVENTION

Figure 4:
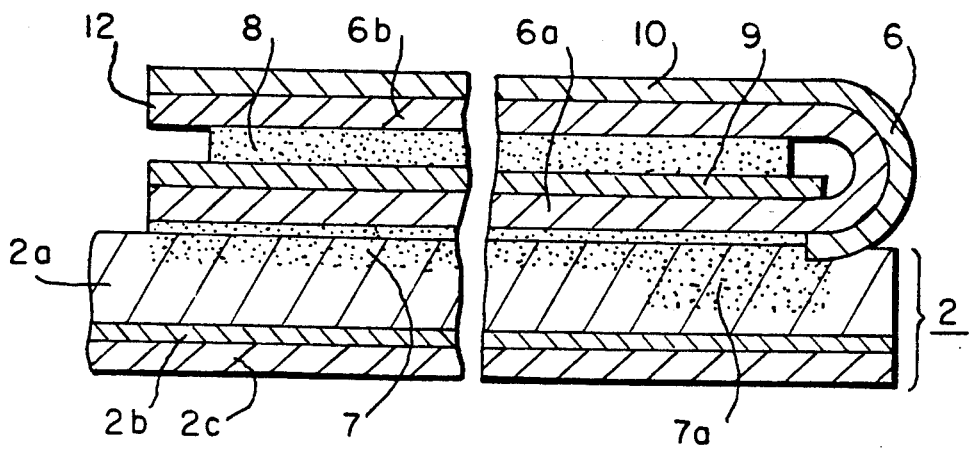
FIG. 4 is an enlarged sectional view taken on line IV—IV of FIG. 1.

The pressure-sensitive tape of the present invention comprises a tape substrate, a first pressure-sensitive adhesive area provided on one side of the tape substrate in a tape substrate part which is close to one end of the tape substrate, and a second pressure-sensitive adhesive area provided on the side opposite the first pressure-sensitive adhesive area one side of the tape substrate in a tape substrate part which is close to the other end of the tape substrate, either or both of the first pressure-sensitive adhesive area and the second pressure-sensitive adhesive area having a strongly adhesive area at an end part thereof to which an external peeling force is to be applied first, and the strongly adhesive area having a peel strength higher than that of the other part of the pressure-sensitive adhesive area.

The pressure-sensitive tape-fixing structure of the present invention comprises a member made of a material having a rough surface, such as a nonwoven fabric, and fixed thereto a pressure-sensitive tape comprising a tape substrate, a first pressure-sensitive adhesive area provided on one side of the tape substrate in a tape substrate part which is close to one end of the tape substrate, and a second pressure-sensitive adhesive area provided on one side of the tape substrate in a tape substrate part which is close to the other end of the tape substrate, at least one of both end parts of the first pressure-sensitive adhesive area which is adjacent to the second pressure-sensitive adhesive area having a pressure-sensitive adhesive layer thickness larger than that in the other part of the first pressure-sensitive adhesive area, and the fixing of the pressure-sensitive tape to the part made of a rough-surface member being established by bonding this first pressure-sensitive adhesive area to the part made of a rough-surface member.

The roll of pressure-sensitive tape of the present invention is obtained by forming a strip comprising a plurality of connected pressure-sensitive tapes and then rolling up this strip, each of the connected pressure-sensitive tapes being as described above.

In the case where a pressure-sensitive tape is peeled off at its first pressure-sensitive adhesive area by an external peeling force, the peeling proceeds from one end to the other end of the first pressure-sensitive adhesive area. In the case where a pressure-sensitive tape is peeled off at its second pressure-sensitive adhesive area by an external peeling force, the peeling proceeds from one end to the other end of the second pressure-sensitive adhesive area. Thus, peeling of the pressure-sensitive adhesive area proceeds from one end to the other end of the pressure-sensitive adhesive area. In other words, the pressure-sensitive adhesive area peels off the adhered from one end to the other end thereof successively.

In the pressure-sensitive tape of the present invention, since the end part of a pressure-sensitive adhesive area to which an external peeling force is to be applied first has a higher peel strength, an external peeling force applied to the pressure-sensitive adhesive area does not peel off the other part of the pressure-sensitive adhesive area so long as the end part having a higher peel strength remains unpeeled. Therefore, although lower in peel strength than the end part, the other part of the pressure-sensitive adhesive area never peels off the adhered first.

Accordingly, the peel strength of the pressure-sensitive tape as a whole can be improved by only increasing the pressure-sensitive adhesive layer thickness in a part of the pressure-sensitive adhesive area, i.e., in the end part, or by otherwise increasing the peel strength of the end part and, hence, there is no need of increasing the pressure-sensitive adhesive layer thickness over the whole pressure-sensitive adhesive area or forming the whole pressure-sensitive adhesive area by using a pressure-sensitive adhesive having high tackiness. Therefore, a pressure-sensitive tape showing improved peel strength when peeled from adhered can be provided without increasing the cost of the production thereof.

In the pressure-sensitive adhesive-fixing structure of the present invention, the depth of the penetration of the pressure-sensitive adhesive of the first pressure-sensitive adhesive area into a part made of a rough-surface member becomes large at the end part of the pressure-sensitive adhesive area which part has a larger pressure-sensitive adhesive layer thickness and, hence, the bonding strength between the first pressure-sensitive adhesive area and the rough-surface member becomes high at that end part. Accordingly, the peel strength of the first pressure-sensitive adhesive area bonded to a rough-surface member can be greatly improved without increasing the thickness of all the first pressure-sensitive adhesive area. This pressure-sensitive tape is particularly useful when applied, for example, to the fastener tape in a diaper in which the second pressure-sensitive adhesive area in the pressure-sensitive tape is repeatedly bonded to and peeled from a part of the diaper while the first pressure-sensitive adhesive area is kept being bonded to a diaper part made of a rough-surface member.

Since the peel strength of the first pressure-sensitive adhesive area bonded to a rough-surface material can be improved without increasing the pressure-sensitive adhesive layer thickness over the whole first pressure-sensitive adhesive area, strong bonding of the pressure-sensitive tape to materials having a rough surface, such as a nonwoven fabric, can be attained without increasing the cost of pressure-sensitive tape production.

The roll of pressure-sensitive tape of the present invention is obtained by forming a strip comprising a plurality of connected pressure-sensitive tapes and then rolling up this strip, each of the connected pressure-sensitive tapes being as described above. Accordingly, a pressure-sensitive tape roll comprising pressure-sensitive tapes having an increased peel strength can be provided without increasing the production cost thereof.

If such a roll of pressure-sensitive tape is constructed as in claim 6, the diameter of the roll on one side thereof and the diameter thereof on the other side can be made almost equal. Therefore, rolling up a strip of such pressure-sensitive tapes and stretching the rolled strip can be conducted surely. Further, this roll of pressure-sensitive tape also has an advantage that its transportation and handling are easy.

Embodiments of the present invention which is applied to a fastener tape in a diaper are described below by reference to accompanying drawings.

Figure 5:
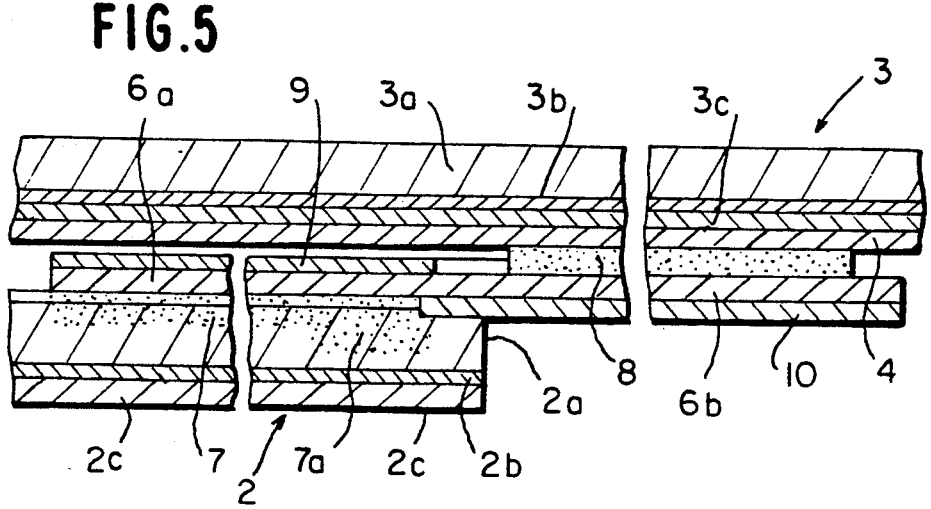
FIG. 5 is an enlarged sectional view taken on line V—V of FIG. 1.

FIGS. 1 to 5 illustrate one embodiment of the present invention. In those FIGURES, numeral 1 denotes a disposable diaper having a back part 2 and a front part 3. As shown in FIGS. 1 and 5, the back part 2 and the front part 3 in the diaper 1 each comprises a top sheet 2a or 3a made of a nonwoven fabric and a back sheet 2c or 3c which is a polyethylene film or the like bonded to the front surface of the top sheet with a hot-melt adhesive 2b or 3b or by other suitable means. To the front surface of the back sheet 3c in the front part 3, a center tape 4 is bonded. A fastener tape 5 as described below is bonded to this center tape 4.

The fastener tape 5 has a tape substrate 6 which is a rectangular film made of polypropylene, polyethylene, poly(ethylene terephthalate), or the like. This tape substrate 6 is double-folded almost at the lengthwise middle. A tape substrate part 6a close to one end of this tape substrate 6 is provided on its outer side (on one side of the tape substrate 6) with a first pressure-sensitive adhesive area 7 which is bonded to the top sheet 2a of the back part 2 in the diaper 1, while a tape substrate part 6b close to the other end of the tape substrate 6 is provided on its inner side (on the other side of the tape substrate 6) with a second pressure-sensitive adhesive area 8 which is bonded to the center tape 4 on the front part 3 in the diaper 1.

The pressure-sensitive adhesive areas 7 and 8 are formed by a conventional pressure-sensitive adhesive such as acrylic type, polyolefin type, rubber type or other types.

Figure 7:
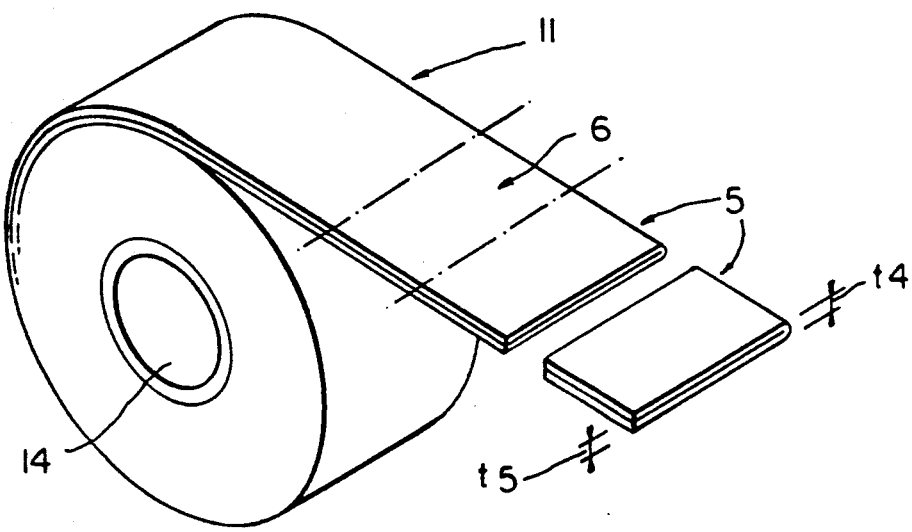
FIG. 7 is a perspective view of a roll of fastener tape which is one embodiment of the pressure-sensitive tape roll according to the present invention.

In the tape substrate 6, the part 6a close to one end of the tape substrate 6 is provided on its inner side with a first release layer 9 for enabling the second pressure-sensitive adhesive area 8 to be peeled from the part 6a. This first release layer 9 is formed by coating a release agent on the part 6a. On the other hand, the tape substrate part 6b close to the other end of the tape substrate 6 is provided on its outer side with a second release layer 10. When a plurality of such pressure-sensitive tapes 5 are formed in a continuous form in which the pressure-sensitive tapes 5 are connected with one another in their width direction, and the resulting strip is wound into a roll 11 as shown in FIG. 7, the second release layer 10 in each pressure-sensitive tape serves to make an overlying first pressure-sensitive adhesive area 7 peelable from the tape substrate part 6b close to the other end of the tape substrate 6.

Release treatment of the tape substrate 6 for forming the release layers 9 and 10 is not limited to the coating of a release agent as described above, and other means may be taken. For example, the tape substrate 6 may be embossed to reduce the adhesion between the tape substrate 6 and the pressure-sensitive adhesive areas 7 and 8.

In the case where the pressure-sensitive tapes 5 are produced as single pieces and are not intended to be formed into a roll, the second release layer 10 is unnecessary and there is no need of double-folding the tape substrate 6. In the case where the pressure-sensitive tapes 5 are produced as single pieces and are not folded, both release layers 9 and 10 are unnecessary.

The other end part of the tape substrate 6 is not provided with the second pressure-sensitive adhesive area 8, and hence is a pressure-sensitive adhesive-free area, thereby constituting a pinch part 12 for use in peeling off the tape substrate part 6b close to this other end part of the tape substrate 6.

Of both end parts of the first pressure-sensitive adhesive area 7, the end part 7a close to the folded part of the tape substrate 6 is further coated with a different pressure-sensitive adhesive 13 to increase the thickness t1 of the end part 7a to a value larger than the thickness t0 of the other part of the first pressure-sensitive adhesive area 7. Thus, the end part 7a in the first pressure-sensitive adhesive area 7 constitutes a strongly adhesive area which adheres more strongly to the nonwoven-fabric top sheet 2a of the back part 2 in the diaper 1 than the other part of the first pressure-sensitive adhesive area 7.

The method of forming the strongly adhesive area at an end part of the pressure-sensitive adhesive area is not limited to a method to partly increase the thickness of the pressure-sensitive adhesive area. The strongly adhesive area may also be formed by using a highly tacky pressure-sensitive adhesive to form the end part and forming the other part of the pressure-sensitive adhesive area from a pressure-sensitive adhesive having lower tackiness, with the thickness of the resulting pressure-sensitive adhesive area being made constant.

The fastener tape 5 having the above-described construction is fixed to the diaper 1 by bonding the first pressure-sensitive adhesive area 7 in the fastener tape 5 to the top sheet 2a of the back part 2 in the diaper 1.

The resulting diaper 1 can be put on an infant or other person by applying the diaper 1 to the body, separating the tape substrate part 6a close to one end of the tape substrate 6 from the tape substrate part 6b close to the other end by pulling the part 6b, and then bonding the separated part 6b to the center tape 4 on the front part 3 with the second pressure-sensitive adhesive area 8.

When the infant or other person who is wearing the diaper 1 moves around or touches the back part 2, or when the second pressure-sensitive adhesive area 8 is temporarily peeled from the center tape 4 in order to refasten the diaper 1 and, as a result, a tensile force is applied to the tape substrate 6, the first pressure-sensitive adhesive area 7 receives an external force which functions to peel off the end part 7a first and the other part of the first pressure-sensitive adhesive area 7 next.

However, since the end part 7a in the first pressure-sensitive adhesive area 7 has a larger thickness than the other part of the first pressure-sensitive adhesive area 7, the pressure-sensitive adhesive in the end part 7a penetrates into the top sheet 2a to a larger depth than that in the other part of the first pressure-sensitive adhesive area 7, and the contact area in which the end part 7a contacts with fibers of the top sheet 2a becomes large. As a result, the bonding strength of the first pressure-sensitive adhesive area 7 to the top sheet 2a becomes high in its end part 7a. In other words, the peel strength of the first pressure-sensitive adhesive area 7 bonded to the top sheet 2a is highest in the end part 7a.

This means that the peel strength of the first pressure-sensitive adhesive area 7 as a whole can be improved by only increasing the peel strength of the end part 7a without increasing the pressure-sensitive adhesive layer thickness over the whole first pressure-sensitive adhesive area 7, because the part of the pressure-sensitive adhesive area 7 other than the end part 7a does not peel off the top sheet 2a so long as the end part 7a remains unpeeled from the top sheet 2a. Therefore, the peel strength of the first pressure-sensitive adhesive area 7 bonded to the top sheet 2a can be improved significantly, that is, the fastener tape 5 can be strongly fixed to the top sheet 2a, without increasing the amount of the pressure-sensitive adhesive used.

Figure 6:
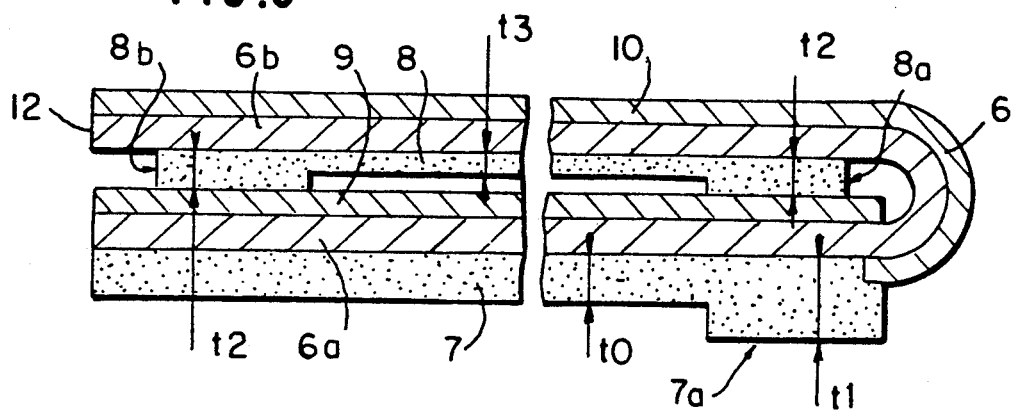
FIG. 6 is a sectional view of another embodiment of the pressure-sensitive tape according to the present invention.

In order that the end part 7a in the first pressure-sensitive adhesive area 7 has a larger thickness than the other part of the first pressure-sensitive adhesive area 7, thereby making the end part 7a to function as a strongly adhesive area, the whole first pressure-sensitive adhesive area 7 may be formed by the same pressure-sensitive adhesive, with only the end part 7a being coated at a larger thickness, as shown in FIG. 6. Alternatively, the end part 7a and the other part of the first pressure-sensitive adhesive area 7 may be formed by separately coating different pressure-sensitive adhesives.

It is also possible to increase the thickness t2 of both end parts 8a and 8b in the second pressure-sensitive adhesive area 8 to a value larger than the thickness t3 of the other part of the second pressure-sensitive adhesive area 8, as shown in FIG. 6, so that the bonding strength of the second pressure-sensitive adhesive area 8 to the center tape 4 becomes large in these end parts 8a and 8b. If the fastener tape is so constructed, the second pressure-sensitive adhesive area 8 can show enhanced peel strength at the initial stage of peeling when the tape substrate part 6b close to the other end of the tape substrate 6 is peeled from the center tape 4. For this reason, even where the infant or other person who is wearing the diaper 1 pulls the pinch part 12 in the tape substrate 6 or moves around, the tape substrate part 6b never peels off the center tape 4 readily.

In the case where the end part 7a in the first pressure-sensitive adhesive area 7 has a larger thickness than the other part to form a strongly adhesive area, it is preferred that in order to obtain peel strength sufficient for strongly fixing the first pressure-sensitive adhesive area 7 to rough-surface members such as a nonwoven fabric, the thickness t1 of the end part 7a is at least 1.1 times, desirably at least 1.3 times, the thickness t0 of the other part of the first pressure-sensitive adhesive area 7, regardless that the strongly adhesive area is formed by using the same pressure-sensitive adhesive or by further coating a different pressure-sensitive adhesive.

FIG. 7 illustrates one embodiment of the roll of the fastener tape according to the present invention.

That is, this embodiment is a pressure-sensitive tape roll 11 obtained by forming a strip comprising a plurality of fastener tapes 5 as described above in which the fastener tapes are connected with one another in their width direction, that is, each of the tape substrate 6, pressure-sensitive adhesive areas 7 and 8, and release layers 9 and 10 is in a continuous form throughout the connected fastener tapes, and then winding this strip on a core 14. By stretching the strip from the roll 11 and cutting it at proper intervals along the lengthwise direction, fastener tapes 5 as shown in FIGS. 1 to 6 can be obtained.

If fastener tapes 5 in which the end part 7a in the first pressure-sensitive adhesive area 7 has a larger thickness than the other part of the first pressure-sensitive adhesive area 7 are formed into a roll 11 as described above, there is a fear that the resulting roll 11 may have a conical shape because the folded fastener tapes 5 have a larger thickness at the part at which the tape substrate 6 is folded and have a smaller thickness at the end part opposite to the folded part.

Figure 8:
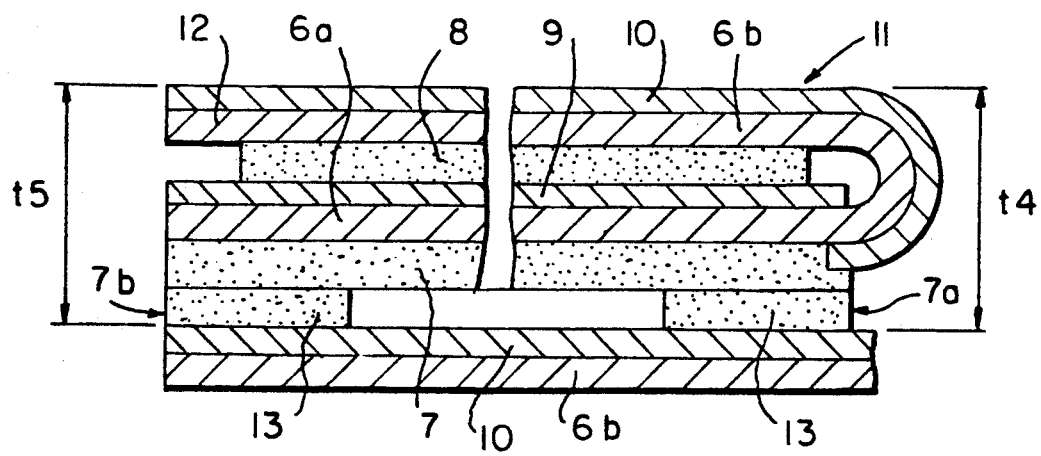
FIG. 8 is a sectional view of a rolled fastener tape which shows another embodiment of the pressure-sensitive tape roll according to the present invention.
Figure 9:
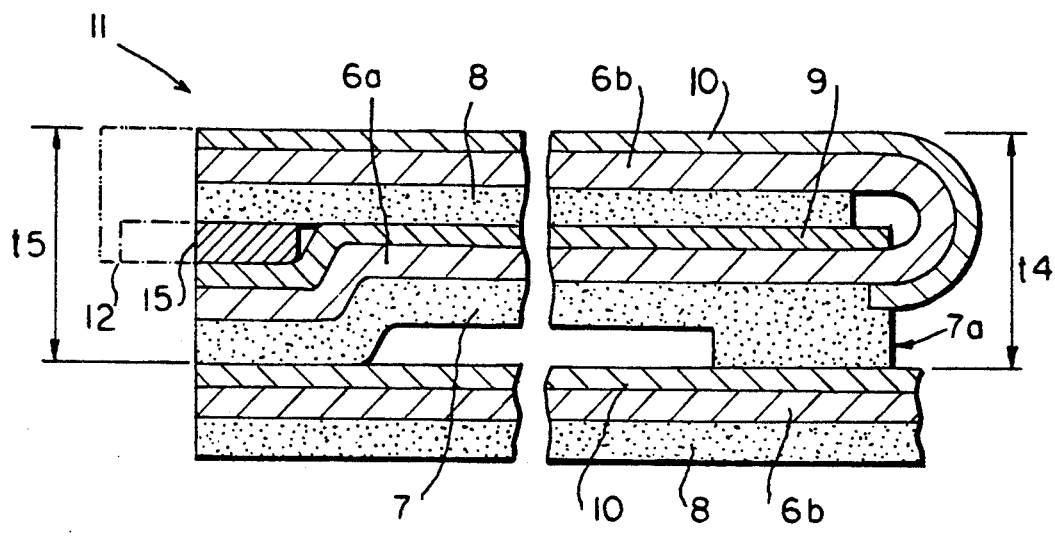
FIG. 9 is a sectional view of a rolled fastener tape which shows still another embodiment of the pressure-sensitive tape roll according to the present invention.
Figure 10:
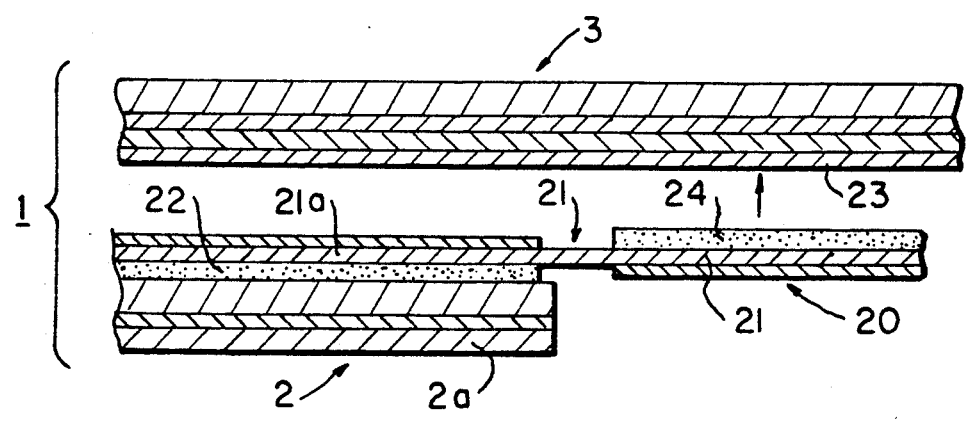
FIG. 10 is a sectional view showing a prior art technique.

This fear can be eliminated by forming the first pressure-sensitive adhesive area 7, so that its end part 7a and other end part 7b have the same thickness as shown in FIG. 8, or by inserting a spacer tape 15 between the second pressure-sensitive adhesive area 8 and the second release layer 10 at the end part opposite to the end part 7a side, as shown in FIG. 9, in a manner such that in the folded fastener tapes in the roll 11, the fastener tape thickness t4 at one side thereof and the fastener tape thickness t5 at the other side come to be almost the same.

In the case of the construction shown in FIG. 9, a pinching part 12 for peeling off the tape substrate part 6b may be formed by inserting the spacer tape 15 in a manner such that it projects outward from the end of the tape substrate 6 as shown by the alternate long and short dash line, or by projecting the tape substrate 6 and the spacer tape 15 outwardly from the end opposite to the end part 7a side as shown by the alternate long and two-short dash line.

Although fastener tapes for diapers are described above as embodiments of the present invention, it is needless to say that the present invention can be applied to other uses such as fastener tapes in disposable aprons. In this case, the position and number of the strongly adhesive area in the fastener tape can be suitably determined by the material of adhered and the use of the apron.

While the invention has been described in detail and with reference to specific embodiments thereof, it will be apparent to one skilled in the art that various changes and modifications can be made therein without departing from the spirit and scope thereof.

What is claimed is:

1. A pressure-sensitive tape fastener comprising:
   (a) tape substrate,
   (b) a first pressure-sensitive adhesive area provided on one side of the tape substrate in a tape substrate part which is close to or at one end of the tape substrate, and
   (c) a second pressure-sensitive adhesive area provided on the side opposite the first pressure-sensitive adhesive area of the tape substrate in a tape substrate part which is close to or at the other end of the tape substrate,
   wherein at least one of said pressure-sensitive adhesive areas has a strongly adhesive area on at least one end segment thereof to which an external peeling force is to be applied first and wherein said strongly adhesive area has a peel strength higher than that of the adjacent segment of lower peel strength of the pressure-sensitive adhesive area.

2. The pressure-sensitive tape of claim 1, wherein said strongly adhesive area is formed by increasing the pressure-sensitive adhesive layer thickness.

3. The pressure-sensitive tape of claim 1, wherein said tape substrate is folded in a manner such that said first pressure-sensitive adhesive area contacts with the other side of a tape substrate part close to or at one end of the tape substrate, and said other side of the tape substrate part close to or at one end of the tape substrate is subjected to a release treatment for enabling said first pressure-sensitive adhesive area to be peeled from said tape substrate part close to or at one end of the tape substrate.

4. A pressure-sensitive tape fastener-fixing structure comprising:
   (1) a member made of a material having a rough surface, having fixed thereto
   (2) a pressure-sensitive tape comprising:
      (a) a tape substrate,
      (b) a first pressure-sensitive adhesive area provided on one side of the tape substrate in a tape substrate part which is close to or at one end of the tape substrate, and
      (c) a second pressure-sensitive adhesive area provided on the side opposite the first pressure-sensitive adhesive area of the tape substrate in a tape substrate part which is close to or at the other end of the tape substrate,
      wherein at least one of both end segment of said first pressure-sensitive adhesive area which is adjacent to said second pressure-sensitive adhesive area has a pressure-sensitive adhesive layer thickness larger than that in the adjacent segment of lower peel strength of the first pressure-sensitive adhesive area, and wherein the pressure-sensitive tape is fixed to the rough-surface member by bonding said first pressure-sensitive adhesive area to said member made of a rough-surface material.

5. A roll of pressure-sensitive tape obtained by forming a strip comprising a plurality of connected pressure-sensitive tapes and then rolling up this strip, each of said connected pressure-sensitive tapes being as claimed in claim 1.

6. A roll of pressure-sensitive tape obtained by preparing a plurality of pressure-sensitive tapes each of which is as claimed in claim 3 and in which the folded part of the tape substrate has a thickness almost equal to that of the end part opposite to the folded part, forming a strip comprising these double-folded pressure-sensitive tapes connected with one another, and then rolling up this strip.

7. The pressure-sensitive tape of claim 1, wherein said strongly adhesive area is formed by using a higher tacky pressure-sensitive adhesive, and wherein the thickness of the pressure sensitive adhesive layer is constant.

8. The pressure-sensitive tape of claim 1, wherein said pressure sensitive adhesive layer is comprised of different coatings of pressure-sensitive adhesives.

9. The pressure-sensitive tape of claim 3, wherein said release treatment is selected from the group consisting of coating a release agent and embossing.

10. The pressure-sensitive tape of claim 3, wherein said second pressure-sensitive adhesive area is provided on a tape substrate part which is close to, but not at the end of the tape substrate and creates a pressure-sensitive adhesive-free area that serves as a pinching part for peeling off the tape substrate end containing the second pressure-sensitive adhesive area.

11. The pressure-sensitive tape-fixing structure of claim 4, wherein the larger thickness area of the first pressure-sensitive adhesive layer is at least 1.1 times thicker than the other part of the first pressure-sensitive adhesive layer.

12. The pressure-sensitive tape-fixing structure of claim 4, wherein the larger thickness area of the first pressure-sensitive adhesive layer is at least 1.3 times thicker than the other part of the first pressure-sensitive adhesive layer.

13. The pressure-sensitive tape-fixing structure of claim 4, wherein the larger thickness area of the first pressure-sensitive adhesive layer is further coated with a different pressure-sensitive adhesive.

14. The roll of pressure-sensitive tape of claim 5, wherein each of the pressure-sensitive adhesive areas are contacted with an area subjected to a release treatment.

15. The pressure-sensitive tape of claim 14, wherein said release treatment is selected from the group consisting of coating a release agent and embossing.

16. The roll of pressure-sensitive tape of claim 6, wherein the side of the tape substrate containing the first pressure-sensitive adhesive area is subjected to a release treatment.

17. The pressure-sensitive tape of claim 16, wherein said release treatment is selected from the group consisting of coating a release agent and embossing.

18. The roll of pressure-sensitive tape of claim 6, wherein the side of the tape substrate containing the first pressure-sensitive adhesive area is coated with a release agent on the surface not containing the first pressure-sensitive adhesive area and on the surface partially underneath the first pressure-sensitive adhesive to enable the tape to be rewound in a stable manner.

19. The roll of pressure-sensitive tape of claim 6, wherein said end part opposite to the folded part contains a spacer tape to increase the thickness to that of thickness of the folded part.

20. The roll of pressure-sensitive tape of claim 19, wherein said spacer tape protrudes from the end part opposite to the folded part to form a pinching part for peeling off the tape substrate end containing the second pressure-sensitive adhesive area.

* * * * *